(12) United States Patent
Zhang et al.

(10) Patent No.: US 11,600,400 B2
(45) Date of Patent: Mar. 7, 2023

(54) DRIVING MECHANISM

(71) Applicant: SHANGHAI UNITED IMAGING HEALTHCARE CO., LTD., Shanghai (CN)

(72) Inventors: Jian Zhang, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 50 days.

(21) Appl. No.: 17/153,909

(22) Filed: Jan. 21, 2021

(65) Prior Publication Data
US 2021/0225548 A1 Jul. 22, 2021

(30) Foreign Application Priority Data

Jan. 21, 2020 (CN) .......................... 202010068560.6

(51) Int. Cl.
*G21K 1/04* (2006.01)
*A61N 5/10* (2006.01)
*F16H 19/00* (2006.01)

(52) U.S. Cl.
CPC ........... *G21K 1/046* (2013.01); *A61N 5/1047* (2013.01); *F16H 19/001* (2013.01)

(58) Field of Classification Search
CPC .. A61B 6/06; A61B 6/40; A61B 90/35; A61N 5/10; A61N 5/104; A61N 5/1042;
(Continued)

(56) References Cited

U.S. PATENT DOCUMENTS 6,823,045 B2 * 11/2004 Kato ........................ G21K 1/04
378/152
2005/0057101 A1 3/2005 Nakagawa et al.
2020/0304045 A1 * 9/2020 Ye ............................. H02P 6/16

FOREIGN PATENT DOCUMENTS

CN 105173684 A 12/2015
CN 106512221 A 3/2017
(Continued)

OTHER PUBLICATIONS

Varitron Brochure: "Drive Technology, FAQ: Coaxial Gearbox (Gear Reducers)", (2014), pp. 1-3 (Found at https://www.c-var.com/faq_show.asp?seq=63&title=Coaxial-Gearbox-Gear-Reducers) (Year: 2014).*

(Continued)

*Primary Examiner* — Don K Wong
(74) *Attorney, Agent, or Firm* — Metis IP LLC

(57) ABSTRACT

The present disclosure provides a driving mechanism configured to drive a target object to perform a linear motion, wherein the target object includes at least one of a plurality of leaves of a multi-leaf collimator. The driving mechanism may include an output component including an output member. The driving mechanism may also include a transmission component configured to operably connect the output component and the target object. The transmission component may include an output end and an input end. The input end may be operably connected with the output member. The output end may be operably connected with the target object. A linear velocity of the output end may be larger than a linear velocity of the input end.

20 Claims, 7 Drawing Sheets

(58) Field of Classification Search
CPC ...... A61N 5/1045; A61N 5/1047; G21K 1/02; G21K 1/04; G21K 1/046; G01N 2223/30; G01N 2223/316; G02B 5/005; G02B 7/00; G02B 7/005; G02B 26/08; G02B 27/09; G02B 27/0938; G02B 27/0988; G02B 27/30; H01J 35/14; H01J 35/16; H01J 37/02; H01J 37/023; H01J 37/08; H01J 37/147; H01J 37/1471; H01J 37/1472; H01J 2237/024; H01J 2237/04; H01J 2237/045; H01J 2237/0455; H01J 2237/0456; H01J 2237/0458; H01J 2237/083; H01J 2237/15; H01J 2237/1502; F16H 19/001; F16H 37/02; F16H 37/04; F16H 37/14; F16H 55/00; F16H 55/02; F16H 55/10; F16H 55/17; F16H 2025/2062; F16H 3/00; F16H 3/002; F16H 3/423; F16H 3/426; F16H 55/171; F16H 55/51; F16H 55/56

See application file for complete search history.

(56) References Cited

FOREIGN PATENT DOCUMENTS

| | | | |
|---|---|---|---|
| CN | 206941153 U | 1/2018 | |
| CN | 208640941 U | 3/2019 | |
| CN | 208997288 U | 6/2019 | |
| CN | 209604500 U | 11/2019 | |
| EP | 1961446 A1 * | 8/2008 | ........... A61N 5/1045 |
| JP | 2004089214 A | 3/2004 | |
| JP | 2010071347 A | 4/2010 | |

OTHER PUBLICATIONS

The Second Office Action in Chinese Application No. 202010068560.6 dated Dec. 30, 2021, 16 pages.

* cited by examiner

300

100

DRIVING MECHANISM

CROSS-REFERENCE TO RELATED APPLICATIONS

This application claims priority to Chinese Patent Application No. 202010068560.6 filed on Jan. 21, 2020, the contents of which are hereby incorporated by reference.

TECHNICAL FIELD

The present disclosure generally relates to a driving mechanism, and in particular, to a driving mechanism for linear motion.

BACKGROUND

Multi-leaf collimators are important mechanical components in linear acceleration collimation systems of modern medical radiotherapy equipment, and mainly used for conformation and intensity modulation of target areas (e.g., including lesions). The multi-leaf collimator includes a plurality of leaves. Each of the plurality of leaves is operably connected to a corresponding driving mechanism, so as to be moved to a corresponding position based on a position command sent by a control system, thereby making the plurality of leaves constitute a shape in equal proportion to a lesion tissue to realize conformation with the target area. The driving mechanism may affect the efficiency of adjusting the multi-leaf collimator to a specific shape. Therefore, it is desirable to provide a driving mechanism having an improved driving efficiency.

SUMMARY

According to a first aspect of the present disclosure, a driving mechanism configured to drive a target object to perform a linear motion may include an output component including an output member. The driving mechanism also include a transmission component configured to operably connect the output component and the target object. The transmission component includes an output end and an input end. The input end is operably connected with the output member. The output end is operably connected with the target object. A linear velocity of the output end is larger than a linear velocity of the input end.

In some embodiments, the input end includes a first gear. The output end includes a second gear.

In some embodiments, the first gear and the second gear is disposed coaxially.

In some embodiments, a radius of the second gear is larger than a radius of the first gear.

In some embodiments, an angular velocity of the first gear may be the same as an angular velocity of the second gear.

In some embodiments, the output member may be driven to perform a driving motion so as to drive the target object to perform the linear motion.

In some embodiments, a motion direction of the linear motion of the target object may be parallel to a motion direction of the driving motion of the output member.

In some embodiments, a motion direction of the linear motion of the target object may be at an angle with a motion direction of the driving motion of the output member.

In some embodiments, within a same time period, a distance of the linear motion may be longer than a distance of the corresponding driving motion.

In some embodiments, the output component may be disposed on a side of the target object that is parallel to a motion direction of the linear motion of the target object.

In some embodiments, the output component may be disposed on a path of the linear motion.

In some embodiments, the output component may include a linear motor. The linear motor may include a stator and a mover. The mover may be linearly movable relative to the stator. The output member may include the mover.

In some embodiments, the output component may include a first gear rack fixedly connected with the output member. The input end may be operably connected with the output member through the first gear rack.

In some embodiments, the input end may include a portion that meshes with the first gear rack.

In some embodiments, the output member may include a bushing and a core. The core may be fixedly connected with an inner surface of the bushing. The first gear rack may be fixedly connected with an outer surface of the bushing.

In some embodiments, the driving mechanism may further include a second gear rack that is fixedly connected with the target object. The output end may be operably connected with the target object through the second gear rack.

In some embodiments, the output end may include a portion that meshes with the second gear rack.

In some embodiments, the target object may include at least one of a plurality of leaves of a multi-leaf collimator.

According to another aspect of the present disclosure, a driving mechanism configured to drive a target object to perform a linear motion may include a linear motor. The linear motor includes a stator, a mover linearly movable relative to the stator, and a gear rack fixedly connected with the mover. The driving mechanism also include a transmission component configured to connect the linear motor and the target object. The transmission component includes an output member and an input end. The input end is operably connected with the mover through the gear rack. The output member is operably connected with the target object. A linear velocity of the output member is larger than a linear velocity of the input end.

According to yet another aspect of the present disclosure, a system includes a multi-leaf collimator including a plurality of leaves, and a driving mechanism configured to drive a target object to perform a linear motion. The target object includes at least one of the plurality of leaves. The driving mechanism includes an output component including an output member. The driving mechanism also include a transmission component configured to operably connect the output component and the target object. The transmission component includes an output end and an input end. The input end is operably connected with the output member. The output end is operably connected with the target object. A linear velocity of the output end is larger than a linear velocity of the input end.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
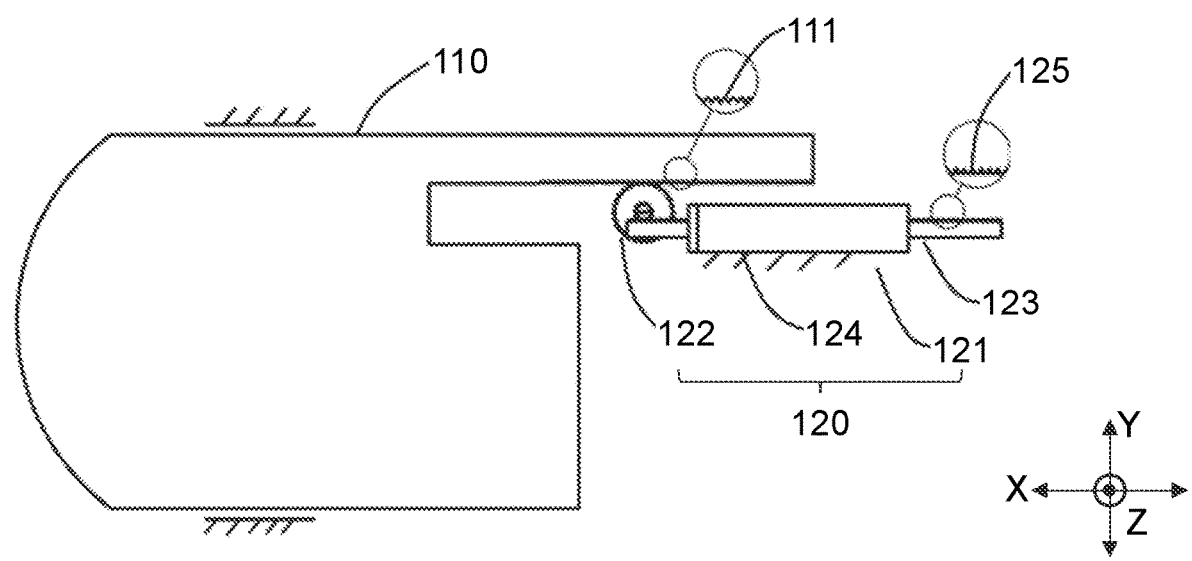
FIG. 1 is a schematic diagram illustrating an exemplary driving system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the disclosed embodiments. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The driving mechanism provided in the present disclosure may be applied in scenarios that need linear motion driving. For brevity, a driving mechanism for a multi-leaf collimator (e.g., a multi-leaf collimator in medical radiotherapy equipment) may be taken as an example in the present disclosure. It should be noted that the driving mechanism for the multi-leaf collimator described below is merely some examples or implementations. For persons having ordinary skills in the art, the driving mechanism in the present disclosure may be applied to other similar situations, such as a hydraulic cylinder, etc.

A driving system may include a target object (e.g., at least one of a plurality of leaves of a multi-leaf collimator) and a driving mechanism configured to drive the target object to perform a linear motion. The driving mechanism may include a linear motor configured to provide a driving force for the linear motion of the target object. The linear motor may include a stator and a mover. The mover may be linearly movable relative to the stator. The mover may be directly connected with the target object. The mover may be driven to perform a driving motion so as to drive the target object to perform a linear motion. The direction of the driving motion of the mover (also referred to as a driving direction) may be parallel to the direction of the linear motion of the target object (also referred to as a target motion direction). In this case, within a same time period, a distance of the linear motion of the target object may be equal to a distance of the corresponding driving motion of the mover.

The size of the driving system in the target motion direction may be related to a motion range of the driving motion of the mover. The larger the motion range of the mover is, the longer the mover may be, the larger the size of the driving system in the target motion direction may be, and the lower the precision of the driving system may be. In order to improve the precision of the driving system, it is desirable to reduce the size of the driving system in the target motion direction.

In the present disclosure, a transmission component is provided to operably connect the target object and the mover. The transmission component may include an output end (e.g., a larger gear) and an input end (e.g., a smaller gear). The input end may be configured to be operably connected with the mover. The output end may be configured to be operably connected with the target object. The transmission component may be configured so that a linear velocity of the output end is larger than a linear velocity of the input end. With the transmission component, within a same time period, a distance of the linear motion of the target object may be longer than a distance of the corresponding driving motion of the mover, which may reduce the motion range of the driving motion of the mover, thereby reducing the size of the driving system in the target motion direction.

Figure 2:
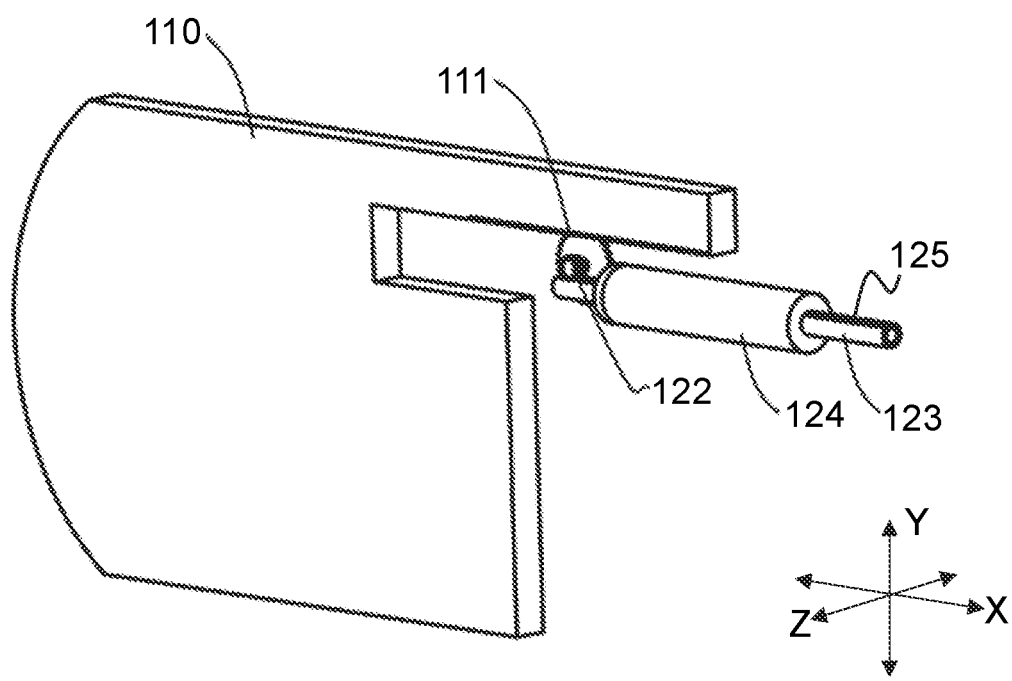
FIG. 2 is a schematic diagram illustrating an exemplary transmission component according to some embodiments of the present disclosure.

FIG. 1 is a schematic diagram illustrating an exemplary driving system 100 according to some embodiments of the present disclosure. FIG. 2 is a schematic diagram illustrating the exemplary driving system 100 seen from a view different from FIG. 1 according to some embodiments of the present disclosure. In the present disclosure, the X direction, the Y direction, and the Z direction shown in FIGS. 1 and 2 may form an orthogonal coordinate system. The Z direction illustrated in FIG. 1 may be vertical to the paper.

In some embodiments, as shown in FIGS. 1 and 2, the driving system 100 may include a target object 110 and a driving mechanism 120 configured to drive the target object 110 to perform a linear motion along a target motion direction (e.g., the X direction shown in FIGS. 1 and 2). In some embodiments, the driving mechanism 120 may include an output component 121 and a transmission component 122 with a distance amplification function. The output component 121 may be configured to perform a driving motion to provide a driving force, so as to drive the target object 110 to perform the linear motion along the X direction. In some embodiments, the driving motion of the output component 121 may be a linear motion. The transmission component 122 configured to operably connect the output component 121 and the target object 110. The transmission component 122 may transmit the driving force from the output component 121 to the target object 110 so as to drive the target object 110 to perform the linear motion along the X direction. In some embodiments, the transmission component 122 may include an output end and an input end. The input end may be operably connected with the output component 121. The output end may be operably connected with the target object 110. In some embodiments, the transmission component 122 may be meshed with the output component 121 and the target object 110.

In some embodiments, a distance of the linear motion of the target object 110 that is operably connected to the output end of the transmission component 122 may be proportional to a linear velocity of the output end of the transmission component 122. For example, the distance of the linear motion of the target object 110 may be equal to the product of the linear velocity of the output end and the motion time of the linear motion. In some embodiments, a distance of the driving motion of the output component 121 that is operably connected to the input end of the transmission component 122 may be proportional to a linear velocity of the input end of the transmission component 122. For example, the distance of the driving motion of the output component 121 may be equal to the product of the linear velocity of the input end and the motion time of the driving motion. In some embodiments, the transmission component 122 may be configured so that a linear velocity of the output end may be larger than a linear velocity of the input end. In this way, within a same time period, a distance of the linear motion of the target object 110 may be longer than a distance of the corresponding driving motion of the output component 121.

In some embodiments, a motion direction of the linear motion of the target object 110 (also referred to as a target motion direction) (e.g., the X direction in FIGS. 1 and 2) may be at any angle with a motion direction of the driving motion of the output component 121 (also referred to as a driving direction). For example, as shown in FIGS. 1 and 2, the target motion direction may be parallel to the driving direction. As another example, the target motion direction may be perpendicular to the driving direction (e.g., the Y direction or the Z direction in FIGS. 1 and 2).

In some embodiments, the output component 121 may include an output member 123 and a stationary member 124. The output member 123 may be linearly movable relative to the stationary member 124. In some embodiments, the input end of the transmission component 122 may be operably connected with the output member 123. The output member 123 may be driven to perform a driving motion so as to drive the target object 110 to perform the linear motion along the X direction. The driving motion of the output member 123 may be designated as the driving motion of the output component 121. The distance of the driving motion of the output member 123 may be designated as the distance of the driving motion of the output component 121. The motion direction of the driving motion of the output member 123 may be designated as the motion direction of the driving motion of the output component 121.

In some embodiments, the output component 121 may further include a first gear rack 125 that is fixedly connected with the output member 123 in a detachable or non-detachable manner. For example, the output member 123 may be integrally formed with the first gear rack 125. As another example, the first gear rack 125 may be welded to the output member 123. The input end may be operably connected with the output member 123 through the first gear rack 125. In some embodiments, the input end may include a portion that meshes with the first gear rack 125.

In some embodiments, a second gear rack 111 may be fixedly connected with the target object 110 in a detachable or non-detachable manner. For example, the target object 110 may be integrally formed with the second gear rack 111. As another example, the second gear rack 111 may be welded to the target object 110. The output end may be operably connected with the target object 110 through the second gear rack 111. In some embodiments, the output end may include a portion that meshes with the second gear rack 111.

In some embodiments, when the first gear rack 125 moves with the output member 123, the first gear rack 125 may drive the transmission component 122 to move. The second gear rack 111 may move with the transmission component 122 to drive the target object 110 to perform a linear motion along the X direction.

In some embodiments, the driving mechanism 120 may further include a housing (not shown). The output component 121 and the transmission component 122 may be positioned within the housing.

In some embodiments, the output component 121 may include a motor. The motor may include a linear motor or a rotary motor. In some embodiments, the linear motor may include a cylindrical linear motor, a U-slot linear motor, a flat linear motor, or the like. In some embodiments, for a linear motor, the stationary member 124 may include a stator. The output member 123 may include a mover. The mover may be linearly movable relative to the stator. Details regarding the linear motor may be found elsewhere in the present disclosure (e.g., the description in connection with FIG. 10).

In some embodiments, the target object 110 may include at least one of a plurality of leaves of a multi-leaf collimator. In some embodiments, the target object 110 may be changed according to different application scenarios. For example, when the driving system 100 is applied in a hydraulic cylinder, the target object 110 may include one or more piston rods.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the transmission component 122 may include a gear assembly. The gear assembly may refer to a device including one or more gears configured to perform force transmission. In some embodiments, the gear assembly may include one or more gears.

Figure 3:
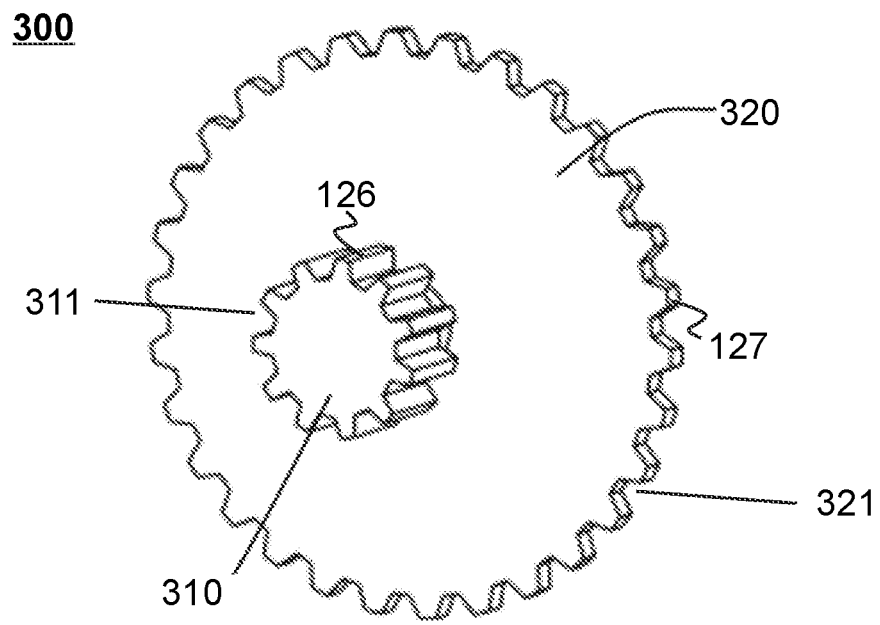
FIG. 3 is a schematic diagram illustrating an exemplary configuration of a transmission component according to some embodiments of the present disclosure.

FIG. 3 is a schematic diagram illustrating an exemplary configuration 300 of the transmission component 122 according to some embodiments of the present disclosure.

As shown in FIG. 3, an input end 311 of the configuration 300 may include a first gear 126. An output end 321 of the configuration 300 may include a second gear 127. In some embodiments, the first gear 126 and the second gear 127 may be disposed coaxially. In some embodiments, a radius of the second gear 127 may be larger than a radius of the first gear 126. In some embodiments, an angular velocity of the first gear 126 may be the same as an angular velocity of the second gear 127. In some embodiments, the second gear 127 may rotate with the first gear 126.

In some embodiments, the first gear 126 and the second gear 127 may be coaxially connected using a rotation shaft. In some embodiments, the first gear 126 may be directly fixed to the second gear 127. For example, a side (e.g., a side without teeth) of the first gear 126 opposite to a side surface 310 of the first gear 126 may be fixedly connected to a side surface 320 of the second gear 127. In some embodiments, the first gear 126 may be fixedly connected to the second gear 127 in a detachable or non-detachable manner. For example, the first gear 126 may be fixedly connected to the second gear 127 in an integrative molding way. As another example, the first gear 126 may be welded to the second gear 127.

In some embodiments, the transmission component 122 with the configuration 300 and the stationary member 124 may be fixedly disposed in the housing of the driving mechanism 120. The output member 123 may be linearly movable relative to the stationary member 124. The first gear 126 and the second gear 127 may be rotatable relative to the housing (also the stationary member 124). In some embodiments, the second gear 127 may be configured to be operably connected with the target object 110. The first gear 126 may be configured to be operably connected with the output member 123. When the first gear rack 125 moves with the output member 123, the first gear rack 125 may drive the first gear 126 to move. The second gear 127 may move with the first gear 126 to drive the second gear rack 111, thereby driving the target object 110 to perform a linear motion.

In some embodiments, the second gear 127 may rotate with the first gear 126. Therefore, the angular velocity of the first gear 126 may be the same as the angular velocity of the second gear 127. For example, within a same time period, the rotation angle of the first gear 126 may be equal to the rotation angle of the second gear 127. In some embodiments, the radius of the first gear 126 may be smaller than the radius of the second gear 127. Therefore, within a same time period, the arc length corresponding to the rotation angle of the first gear 126 (the arc length=the corresponding rotation angle x the corresponding radius) may be shorter than the arc length corresponding to the rotation angle of the second gear 127.

In some embodiments, when the output member 123 performs a driving motion with a distance equal to the circumference of the first gear 126, the output member 123 may drive the first gear 126 to rotate for one turn. The second gear 127 may rotate with the first gear 126 for one turn. The target object 110 may be driven to perform, along the X direction, a linear motion with a distance equal to the circumference of the second gear 127. The ratio of the distance of the driving motion of the output member 123 to the distance of the linear motion of the target object 110 may be equal to the ratio of the circumference of the first gear 126 to the circumference of the second gear 127. That is, the ratio of the distance of the driving motion of the output member 123 to the distance of the linear motion of the target object 110 may be equal to the ratio of the radius of the first gear 126 to the radius of the second gear 127. In some embodiments, the radius of the first gear 126 or the second gear 127 may refer to a reference radius of the first gear 126 or the second gear 127.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 4:
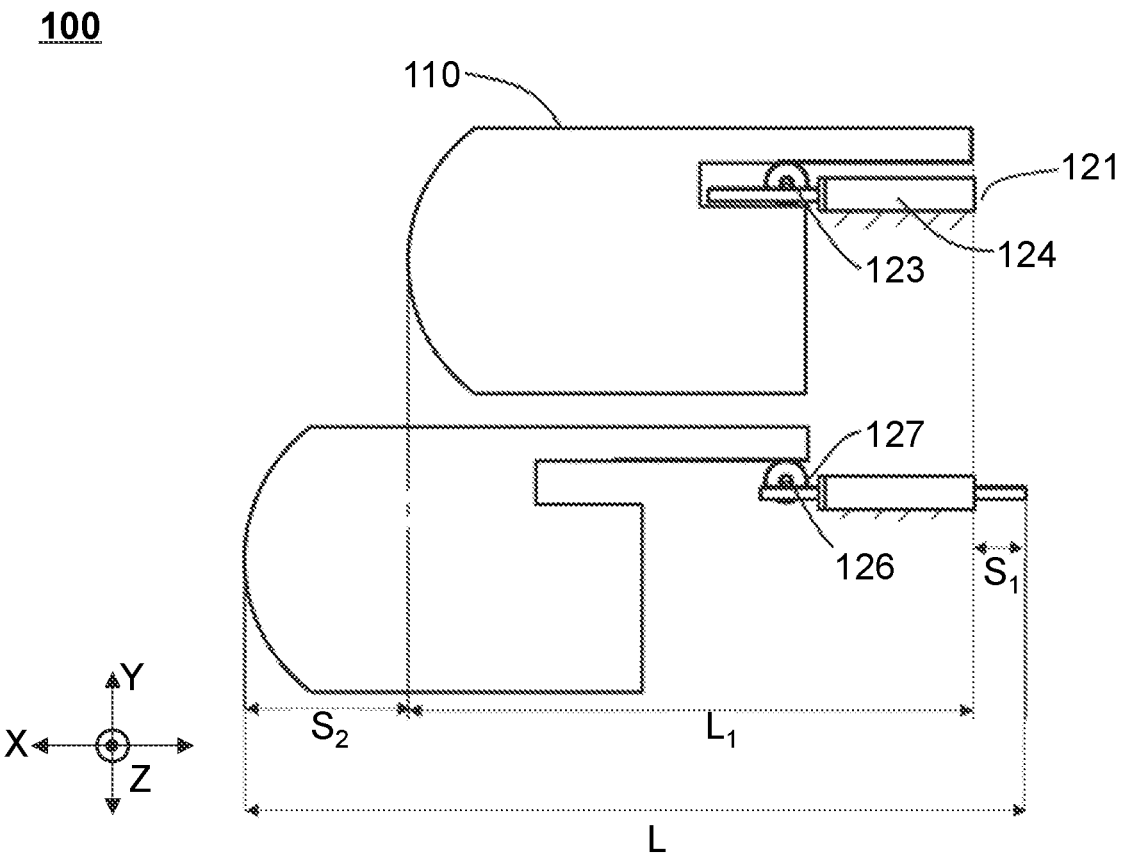
FIG. 4 is a schematic diagram illustrating a size of an exemplary driving system in a target motion direction according to some embodiments of the present disclosure.

FIG. 4 is a schematic diagram illustrating a size of the exemplary driving system 100 in a target motion direction according to some embodiments of the present disclosure. The X direction, the Y direction, and the Z direction in FIG. 4 may correspond to those in FIG. 1.

In some embodiments, a size of the driving system 100 in a target motion direction (e.g., the X direction) of the target object 110 may relate to a maximum motion range of the target object 110, a maximum motion range of the output member 123 in the target motion direction, and a static size of the driving system 100. For example, the larger the maximum motion range of the target object 110 is, the larger the size of the driving system 100 in the target motion direction may be. As another example, the larger the maximum motion range of the output member 123 in the target motion direction is, the larger the size of the driving system 100 in the target motion direction may be. As still another example, the larger the static size of the driving system 100 is, the larger the size of the driving system 100 in the target motion direction may be.

In some embodiments, the static size of the driving system 100 may relate to sizes of the target object 110 and the stationary member 124 in the target motion direction. For example, the larger the size of the target object 110 in the target motion direction is, the larger the static size of the driving system 100 may be. As another example, the larger the size of the stationary member 124 in the target motion direction is, the larger the static size of the driving system 100 may be.

Merely by way of example, as shown in FIG. 4, the size L of the driving system 100 in the target motion direction (e.g., the X direction) may be equal to a sum of the maximum motion range $S_2$ of the target object 110, the maximum motion range $S_1$ of the output member 123 in the target motion direction, and the static size $L_1$ of the driving system 100, i.e., $L=L_1+S_1+S_2$.

In some embodiments, under the condition that the maximum motion range $S_2$ of the target object 110 and the static size $L_1$ of the driving system 100 remain unchanged, the smaller the maximum motion range $S_2$ of the output member 121 in the target motion direction is, the smaller the size of the driving system 100 in the target motion direction may be.

In some embodiments, the larger the size of the driving system 100 in the target motion direction is, the lower the precision of the driving system 100 may be. Therefore, through the transmission component 122 with a distance amplification function, the maximum motion range of the output member 121 may be smaller than the maximum motion range of the target object 110, which may reduce the size of the driving system 100 in the target motion direction, thereby improving the precision of the driving system 100.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the configuration of the driving mechanism may be adjusted to reduce the size of the driving system in the target motion direction. For example, the driving mechanism may be configured so that at least a portion of the length of the stationary member in the target motion direction overlaps at least a portion of the length of the target object in the target motion direction, which may reduce the static size of the driving system, thereby reducing the size of the driving system in the target motion direction. As another example, the driving mechanism may be configured so that the driving direction of the output member may be at a specific angle with the target motion direction of the target motion direction, which may reduce the occupation, in the target motion direction, of the motion range of the output member, thereby reducing the size of the driving system in the target motion direction.

Figure 5:
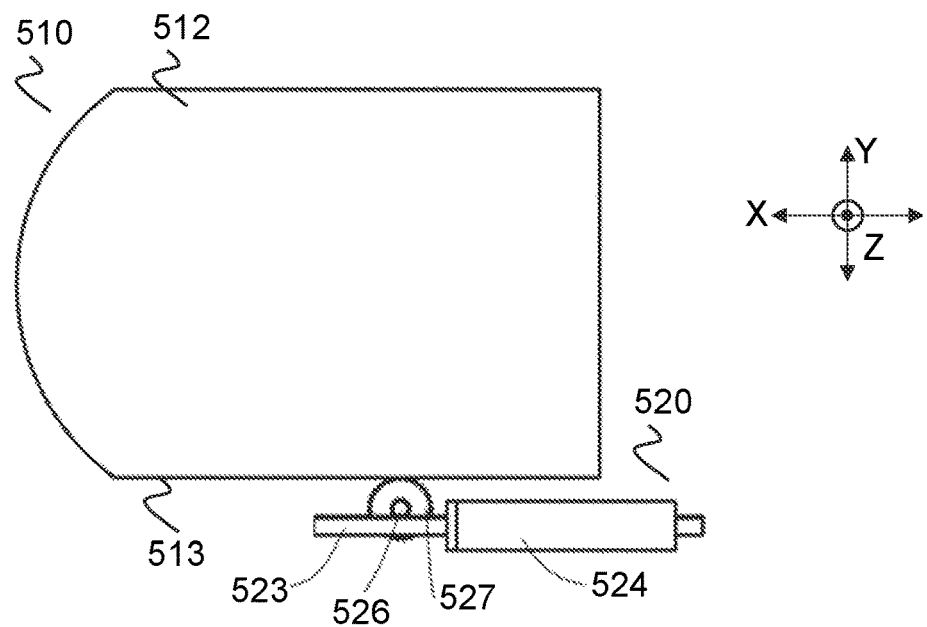
FIG. 5 is a schematic diagram illustrating an exemplary driving system according to some embodiments of the present disclosure.

In some embodiments, the driving mechanism may be disposed on a side (e.g., a side 512, a side opposite to the side 512, a side 513, or a side opposite to the side 513 of the target object 510 in FIG. 5) of the target object that is parallel to the target motion direction (e.g., the X direction in FIG. 5) so that at least a portion of the length of the stationary member in the target motion direction overlaps at least a portion of the length of the target object in the target motion direction, which may reduce the static size of the driving system, thereby reducing the size of the driving system in the target motion direction.

In some embodiments, the driving mechanism may be disposed on a path of the linear motion of the target object so that at least a portion of the length of the stationary member in the target motion direction overlaps at least a portion of the length of the target object in the target motion direction, which may reduce the static size of the driving system, thereby reducing the size of the driving system in the target motion direction. For example, as shown in FIGS. 1 and 2, the target object 110 may include a groove. The driving mechanism 120 may be disposed in the groove, so that the driving mechanism 120 may be disposed on a path of the linear motion of the target object 110.

In some embodiments, the transmission component with a distance amplification function may be used in combination with the adjustment of the configuration of the driving mechanism to reduce the size of the driving system in the target motion direction. In some embodiments, when the configuration of the driving mechanism is adjusted to reduce the size of the driving system in the target motion direction, the driving system may not be configured with distance enlargement. For example, the maximum motion range of the target object may be equal to the maximum motion range of the output member.

FIG. 5 is a schematic diagram illustrating an exemplary driving system 500 according to some embodiments of the present disclosure. The X direction, the Y direction, and the Z direction in FIG. 5 may correspond to those in FIG. 1.

As shown in FIG. 5, the driving system 500 may include a target object 510 and a driving mechanism 520 configured to drive the target object 510 to perform a linear motion along a target motion direction (e.g., the X direction shown in FIG. 5). The driving mechanism 520 may include an output component and a transmission component with a distance amplification function. The output component may be configured to provide a driving force, so as to drive the target object 510 to perform a linear motion along the X direction. The transmission component may be configured to operably connect the output component and the target object 510. The output component may include an output member 523 and a stationary member 524. The output member 523 may be linearly movable relative to the stationary member 524 and configured to perform a driving motion to provide a driving force for the linear motion of the target object 510. The transmission component may include a first gear 526 operably connected with the output member 523 and a second gear 527 operably connected with the target object 510.

As shown in FIG. 5, the driving mechanism 520 may be disposed on a side 513 of the target object 510 that is parallel to the target motion direction (e.g., the X direction in FIG. 5). For example, a second gear rack may be fixedly connected with the side 513 of the target object 510. The second gear 527 may be operably connected with the second gear rack. As shown in FIG. 5, the driving direction of the output member 523 may be parallel to the target motion direction. In this way, at least a portion of the length of the stationary member 524 in the target motion direction may overlap at least a portion of the length of the target object 510 in the target motion direction, which may reduce the static size of the driving system 500, thereby reducing the size of the driving system 500 in the target motion direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the driving mechanism 520 may be disposed on a side opposite to the side 513 of the target object 510.

Figure 6:
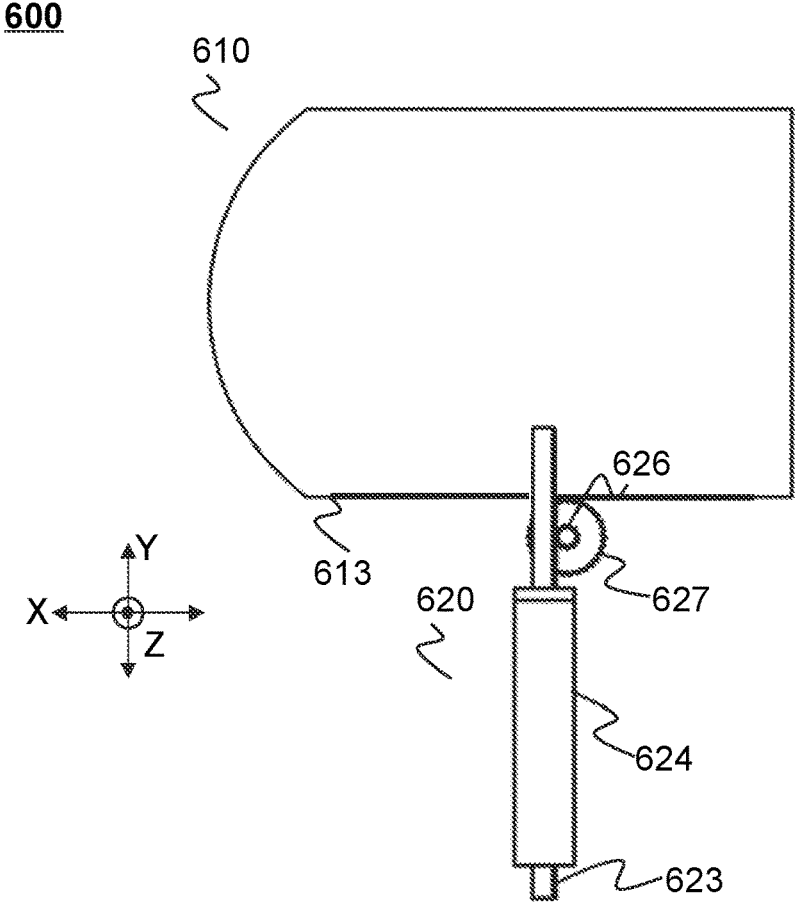
FIG. 6 is a schematic diagram illustrating an exemplary driving system according to some embodiments of the present disclosure.

FIG. 6 is a schematic diagram illustrating an exemplary driving system 600 according to some embodiments of the present disclosure. The X direction, the Y direction, and the Z direction in FIG. 6 may correspond to those in FIG. 1.

As shown in FIG. 6, the driving system 600 may include a target object 610 and a driving mechanism 620 configured to drive the target object 610 to perform a linear motion along a target motion direction (e.g., the X direction shown in FIG. 6). The driving mechanism 620 may include an output component and a transmission component with a distance amplification function. The output component may be configured to provide a driving force, so as to drive the target object 610 to perform a linear motion along the X direction. The transmission component may be configured to operably connect the output component and the target object 610. The output component may include an output member 623 and a stationary member 624. The output member 623 may be linearly movable relative to the stationary member 624 and configured to perform a driving motion to provide a driving force for the linear motion of the target object 610. The transmission component may include a first gear 626 operably connected with the output member 623 and a second gear 627 operably connected with the target object 610.

As shown in FIG. 6, the driving mechanism 620 may be disposed on a side 613 (e.g., corresponding to the side 513 of the target object 510 in FIG. 5) of the target object 610 that is parallel to the target motion direction (e.g., the X direction in FIG. 6). For example, a second gear rack may be fixedly connected with the side 613 of the target object 610. The second gear 627 may be operably connected with the second gear rack. As shown in FIG. 6, the driving direction (e.g., the Y direction in FIG. 6) of the output member 623 may be perpendicular to the target motion direction. In this way, the length of the stationary member 624 in the target motion direction may fall within the length of the target object 510 in the target motion direction, so that the size of the stationary member 624 may not affect the static size of the driving system 600, which may reduce the static size of the driving system 600, thereby reducing the size of the driving system 600 in the target motion direction. In addition, because the driving direction of the output member 623 is perpendicular to the target motion direction, the motion range of the output member 623 may not occupy the size of the driving system 600 in the target motion direction, which may further reduce the size of the driving system 600 in the target motion direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the driving mechanism 620 may be disposed on a side opposite to the side 613 of the target object 610.

Figure 7:
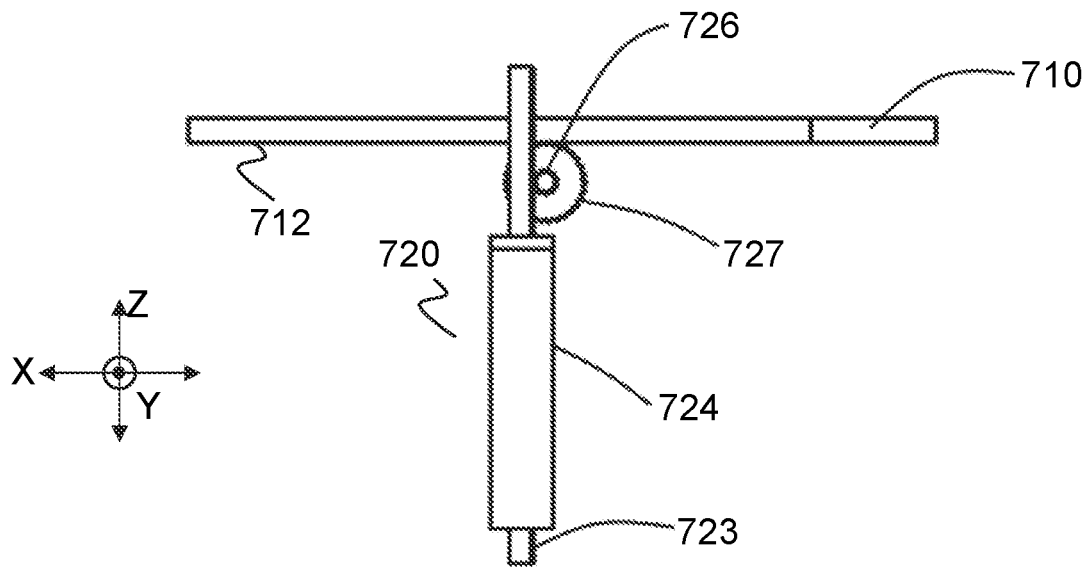
FIGS. 7 and 8 are schematic diagrams illustrating an exemplary driving system according to some embodiments of the present disclosure.
Figure 8:
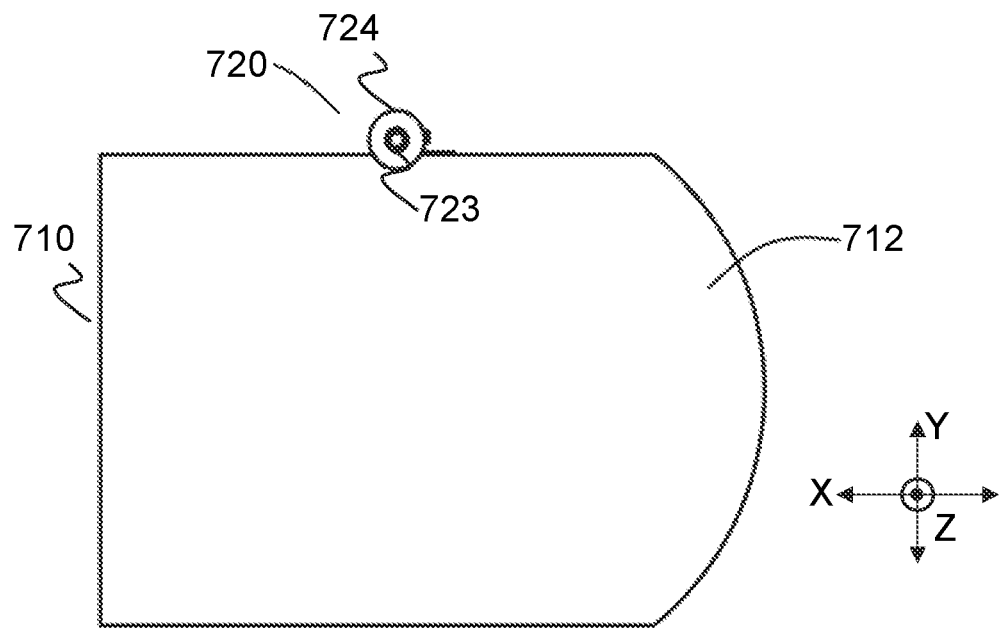

FIG. 7 is a schematic diagram illustrating an exemplary driving system 700 according to some embodiments of the present disclosure. The X direction, the Y direction, and the Z direction in FIG. 7 may correspond to those in FIG. 1. FIG. 8 is a schematic diagram illustrating the exemplary driving system 700 seen from the Y direction in FIG. 7 according to some embodiments of the present disclosure. The X direction, the Y direction, and the Z direction in FIG. 8 may correspond to those in FIG. 7.

As shown in FIGS. 7 and 8, the driving system 700 may include a target object 710 and a driving mechanism 720 configured to drive the target object 710 to perform a linear motion along a target motion direction (e.g., the X direction shown in FIGS. 7 and 8). The driving mechanism 720 may include an output component and a transmission component with a distance amplification function. The output component may be configured to provide a driving force, so as to drive the target object 710 to perform a linear motion along the X direction. The transmission component may be configured to operably connect the output component and the target object 710. The output component may include an output member 723 and a stationary member 724. The output member 723 may be linearly movable relative to the stationary member 724 and configured to perform a driving motion to provide a driving force for the linear motion of the target object 710. The transmission component may include a first gear 726 operably connected with the output member 723 and a second gear 727 operably connected with the target object 710.

As shown in FIGS. 7 and 8, the driving mechanism 720 may be disposed on a side 712 (e.g., corresponding to the side 512 of the target object 510 in FIG. 5) of the target object 710 that is parallel to the target motion direction (e.g., the X direction in FIG. 7). For example, a second gear rack may be fixedly connected with the side 712 of the target object 710. The second gear 727 may be operably connected with the second gear rack. As shown in FIG. 7, the driving direction (e.g., the Z direction in FIGS. 7 and 8) of the output member 723 may be perpendicular to the target motion direction. In this way, the length of the stationary member 724 in the target motion direction may fall within the length of the target object 710 in the target motion direction, so that the size of the stationary member 724 may not affect the static size of the driving system 700, which may reduce the static size of the driving system 700, thereby reducing the size of the driving system 700 in the target motion direction. In addition, because the driving direction of the output member 723 is perpendicular to the target motion direction, the motion range of the output member 723 may not occupy the size of the driving system 700 in the target motion direction, which may further reduce the size of the driving system 700 in the target motion direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the driving mechanism 720 may be disposed on a side opposite to the side 712 of the target object 710.

Figure 9:
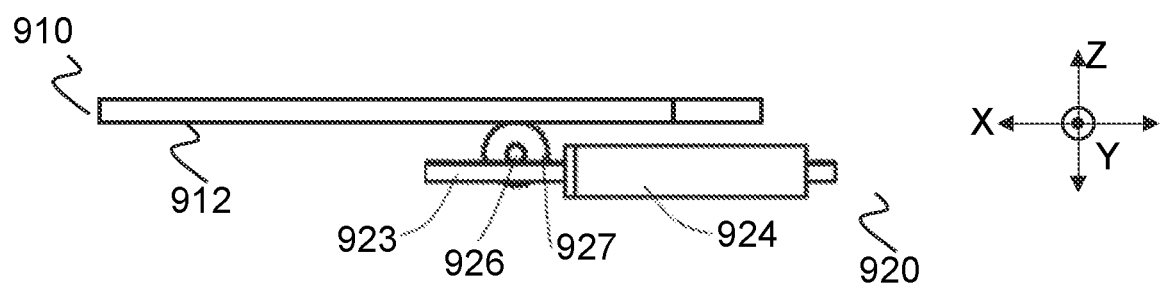
FIG. 9 is a schematic diagram illustrating an exemplary driving system according to some embodiments of the present disclosure.

FIG. 9 is a schematic diagram illustrating an exemplary driving system 900 according to some embodiments of the present disclosure. The X direction, the Y direction, and the Z direction in FIG. 9 may correspond to those in FIG. 1.

As shown in FIG. 9, the driving system 900 may include a target object 910 and a driving mechanism 920 configured to drive the target object 910 to perform a linear motion along a target motion direction (e.g., the X direction shown in FIG. 9). The driving mechanism 920 may include an output component and a transmission component with a distance amplification function. The output component may be configured to provide a driving force, so as to drive the target object 910 to perform a linear motion along the X direction. The transmission component may be configured to operably connect the output component and the target object 910. The output component may include an output member 923 and a stationary member 924. The output member 923 may be linearly movable relative to the stationary member 924 and configured to perform a driving motion to provide a driving force for the linear motion of the target object 910. The transmission component may include a first gear 926 operably connected with the output member 923 and a second gear 927 operably connected with the target object 910.

As shown in FIG. 9, the driving mechanism 920 may be disposed on a side 912 (e.g., corresponding to the side 712 of the target object 710 in FIGS. 7 and 8) of the target object 910 that is parallel to the target motion direction (e.g., the X direction in FIG. 9). For example, a second gear rack may be fixedly connected with the side 912 of the target object 910. The second gear 927 may be operably connected with the second gear rack. As shown in FIG. 9, the driving direction 9 of the output member 623 may be parallel to the target motion direction. In this way, at least a portion of the length of the stationary member 924 in the target motion direction may overlap at least a portion of the length of the target object 910 in the target motion direction, which may reduce the static size of the driving system 900, thereby reducing the size of the driving system 900 in the target motion direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the driving mechanism 920 may be disposed on a side opposite to the side 912 of the target object 910.

Figure 10:
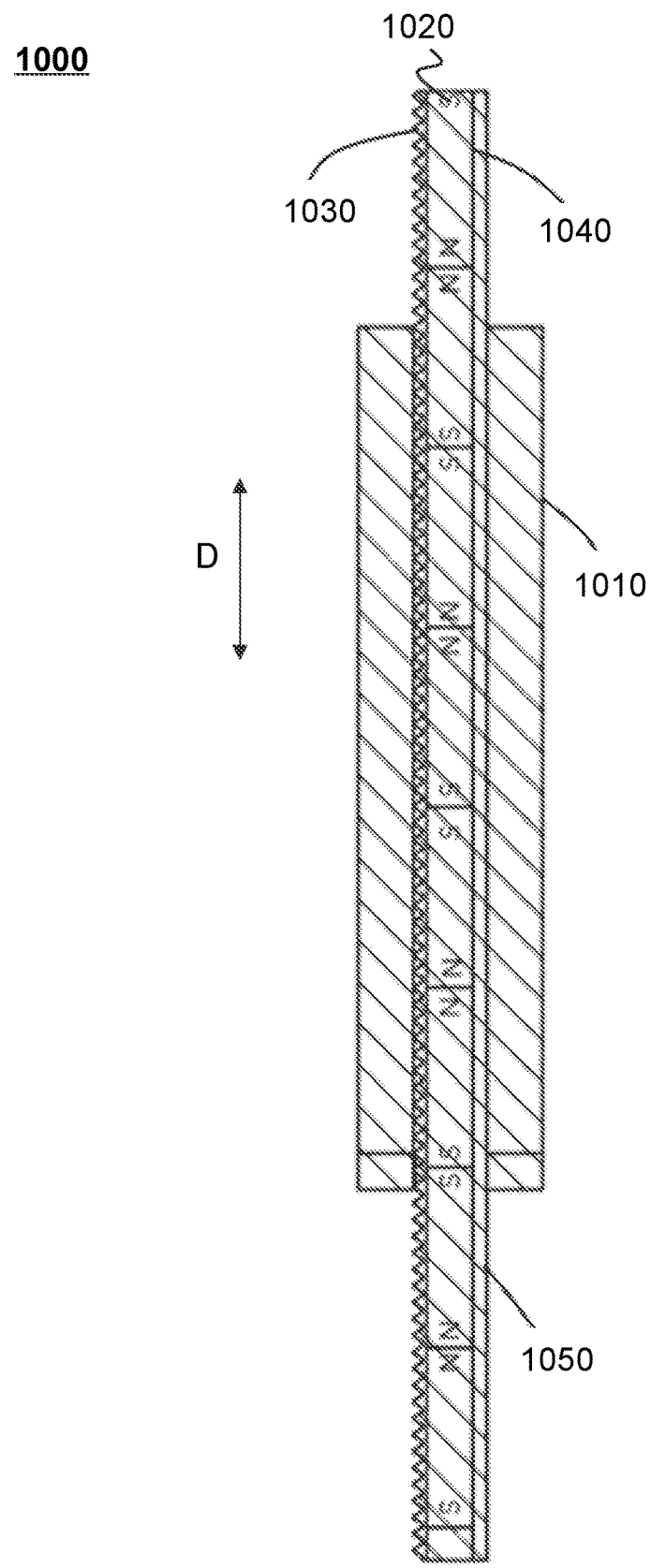
FIG. 10 is a schematic diagram illustrating an exemplary linear motor according to some embodiments of the present disclosure.

FIG. 10 is a schematic diagram illustrating an exemplary linear motor 1000 according to some embodiments of the present disclosure. As shown in FIG. 10, the linear motor 1000 may include a stator 1010, a mover 1020 that is linearly movable relative to the stator 1010, and a first gear rack 1030 that is fixedly connected with the mover 1020.

In some embodiments, the linear motor 1000 may further include a stator coil. The stator coil may refer to a coil disposed on the stator 1010, such as a copper coil wound on the stator 1010. The stator coil may be used as a conductor for energizing the linear motor 1000. The stator 1010 may generate a traveling wave magnetic field when the stator coil is energized. The mover 1020 may induce an electromotive force and generate a current under the cutting of the traveling wave magnetic field. The current may interact with the magnetic field in the air gap of the linear motor 1000 to generate an electromagnetic thrust, thereby driving the mover 1020 to perform a driving motion along, e.g., the D direction in FIG. 10.

Merely by way of example, the output component 121 of the driving system 100 in FIG. 1 may be implemented based on the linear motor 1000. During the movement of the mover 1020, since the first gear rack 1030 may be fixed connected with the mover 1020, and the first gear rack 1030 may be operably connected with the transmission component 122, the linear motor 1000 may transmit, through the first gear rack 1030, the driving force caused by the driving motion of the mover 1020 to the transmission component 122, and then the transmission component 122 may transmit the driving force to the target object 110 to drive the target object 110 to perform a linear motion along a target motion direction (e.g., the X direction in FIG. 1). In some embodiments, the air gap of the linear motor 1000 may refer to the gap between the stator 1010 and the mover 1020.

In some embodiments, the linear motor 1000 may include a cylindrical linear motor. The mover 1020 may have a cylindrical structure, and the stator 1010 may include a track for the mover 1020 to move. In some embodiments, the linear motor 1000 may include motors of other types, such as a U-slot linear motor, a flat-plate linear motor, etc.

In some embodiments, the stator 1010 may further include a stator core and a frame. The frame may be configured to fix the stator core. The stator core may be configured to form a complete magnetic circuit of the linear motor 1000 with the mover 1020 and the air gap.

In some embodiments, the mover 1020 may include a bushing 1050 and a mover core 1040. The mover core 1040 may be fixedly connected with an inner surface of the bushing 1050. The first gear rack 1030 may be fixedly connected with an outer surface of the bushing 1050. When the linear motor 1000 is energized, the stator coil may generate a traveling wave magnetic field. When the mover core 1040 is cut by the traveling wave magnetic field, an electromotive force may be induced and a current may be generated. The current may interact with the magnetic field in the air gap of the linear motor 1000 to generate an electromagnetic thrust, thereby driving the mover core 1040 and the bushing 1050 to perform a driving motion along the D direction in FIG. 10.

In some embodiments, the first gear rack 1030 may be fixedly connected with the outer surface of the bushing 1050 along the longitudinal direction (e.g., the D direction in FIG. 10) of the bushing 1050. In some embodiments, the longitudinal direction of the bushing 1050 may be the same as the motion direction of the driving motion of the mover 1020. In some embodiments, the length of the first gear rack 1030 may be equal to or shorter than the length of the bushing 1050.

In some embodiments, the first gear rack 1030 may be fixedly connected with the bushing 1050 in a detachable or non-detachable manner. For example, the bushing 1050 may be integrally formed with the first gear rack 1030 on the outer surface of the bushing 1050. For instance, the outer surface of the bushing 1050 may be processed to form a plurality of teeth on the outer surface of the bushing 1050 to form the first gear rack 1030. As another example, the first gear rack 1030 may be welded to the outer surface of the bushing 1050. As still another example, the first gear rack 1030 may be fixedly connected with the bushing 1050 in a screw connection, a snap connection, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A driving mechanism configured to drive a target object to perform a linear motion, comprising:
    an output component including an output member, wherein the output member is configured to perform a linear driving motion; and
    a transmission component configured to operably connect the output component and the target object and transmit the linear driving motion of the output member to the linear motion of the target object, the transmission component including an output end and an input end, wherein
        the input end includes a first gear and is operably connected with the output member,
        the output end includes a second gear and is operably connected with the target object, a radius of the second gear being larger than a radius of the first gear, and
        a linear velocity of the output end is larger than a linear velocity of the input end.

2. The driving mechanism of claim 1, wherein the first gear and the second gear are disposed coaxially.

3. The driving mechanism of claim 1, wherein an angular velocity of the first gear is the same as an angular velocity of the second gear.

4. The driving mechanism of claim 1, wherein a motion direction of the linear motion of the target object is parallel to a motion direction of the linear driving motion of the output member.

5. The driving mechanism of claim 1, wherein a motion direction of the linear motion of the target object is at an angle with a motion direction of the linear driving motion of the output member.

6. The driving mechanism of claim 1, wherein, within a same time period, a distance of the linear motion of the target object is longer than a distance of the corresponding linear driving motion of the output member.

7. The driving mechanism of claim 1, wherein the output component is disposed on a side of the target object that is parallel to a motion direction of the linear motion of the target object.

8. The driving mechanism of claim 1, wherein the output component is disposed on a path of the linear motion.

9. The driving mechanism of claim 1, wherein the output component includes a linear motor, the linear motor including a stator and a mover, the mover being linearly movable relative to the stator, the output member including the mover.

10. The driving mechanism of claim 1, wherein the output component includes a first gear rack fixedly connected with the output member, the input end being operably connected with the output member through the first gear rack.

11. The driving mechanism of claim 10, wherein the input end includes a portion that meshes with the first gear rack.

12. The driving mechanism of claim 10, wherein the output member includes a bushing and a core, the core being fixedly connected with an inner surface of the bushing, the first gear rack being fixedly connected with an outer surface of the bushing.

13. The driving mechanism of claim 1, further comprising a second gear rack that is fixedly connected with the target object, wherein the output end is operably connected with the target object through the second gear rack.

14. The driving mechanism of claim 13, wherein the output end includes a portion that meshes with the second gear rack.

15. The driving mechanism of claim 1, wherein the target object includes at least one of a plurality of leaves of a multi-leaf collimator.

16. A driving mechanism configured to drive a target object to perform a linear motion, comprising:
    a linear motor including
        a stator,
        a mover linearly movable relative to the stator, and
        a gear rack fixedly connected with the mover; and
    a transmission component configured to connect the linear motor and the target object, the transmission component including an output end and an input end, wherein
        the input end includes a first gear and is operably connected with the mover through the gear rack,
        the output end includes a second gear and is operably connected with the target object, a radius of the second gear is larger than a radius of the first gear, and
        a linear velocity of the output end is larger than a linear velocity of the input end.

17. A system, comprising:
    a multi-leaf collimator including a plurality of leaves; and
    a driving mechanism configured to drive a target object to perform a linear motion, the target object including at least one of the plurality of leaves, the driving mechanism including:
        an output component including an output member, wherein the output member performs a linear driving motion; and
        a transmission component configured to operably connect the output component and the target object and transmit the linear driving motion of the output member to the linear motion of the target object, the transmission component including an output end and an input end, wherein the input end includes a first gear and is operably connected with the output member, the output end includes a second gear and is operably connected with the target object, a radius of the second gear is larger than a radius of the first gear, and a linear velocity of the output end is larger than a linear velocity of the input end.

18. The driving mechanism of claim 9, wherein the first gear is operably connected with the mover.

19. The driving mechanism of claim 10, wherein the first gear is operably connected with the first gear rack.

20. The driving mechanism of claim 13, wherein the second gear is operably connected with the second gear rack.

\* \* \* \* \*